United States Patent
Balaban et al.

(10) Patent No.: US 6,229,911 B1
(45) Date of Patent: May 8, 2001

(54) METHOD AND APPARATUS FOR PROVIDING A BIOINFORMATICS DATABASE

(75) Inventors: David J. Balaban, San Rafael; Arun Aggarwal, Mountain View, both of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/122,167

(22) Filed: Jul. 24, 1998

Related U.S. Application Data

(60) Provisional application No. 60/069,436, filed on Dec. 11, 1997, provisional application No. 60/069,198, filed on Dec. 11, 1997, and provisional application No. 60/053,842, filed on Jul. 25, 1997.

(51) Int. Cl.[7] ............................................... G06K 9/00
(52) U.S. Cl. ............................ 382/128; 435/6; 356/39; 377/10
(58) Field of Search .................................. 382/128, 129; 435/6; 422/68

(56) References Cited

U.S. PATENT DOCUMENTS

| | | | |
|---|---|---|---|
| 4,683,202 | 7/1987 | Mullis | 435/91.2 |
| 5,143,854 | 9/1992 | Pirrung et al. | 436/518 |
| 5,206,137 | 4/1993 | Ip et al. | 435/6 |
| 5,445,934 | 8/1995 | Fodor et al. | 435/6 |
| 5,492,806 | 2/1996 | Drmanac et al. | 435/5 |
| 5,525,464 | 6/1996 | Drmanac et al. | 435/6 |
| 5,571,639 | 11/1996 | Hubbell et al. | 430/5 |
| 5,593,839 * | 1/1997 | Hubbell et al. | 435/6 |
| 5,667,972 | 9/1997 | Drmanac et al. | 435/6 |
| 5,695,940 | 12/1997 | Drmanac et al. | 435/6 |
| 5,700,637 | 12/1997 | Southern | 435/6 |
| 5,707,806 | 1/1998 | Shuber | 435/5 |
| 5,777,888 | 7/1998 | Rine et al. | 702/19 |
| 5,800,992 * | 9/1998 | Fodor et al. | 435/6 |
| 5,843,767 | 12/1998 | Beattie | 43/4 |
| 5,856,101 * | 1/1999 | Hubbell et al. | 435/6 |
| 5,871,697 | 2/1999 | Rothberg et al. | 422/68.1 |
| 5,871,928 * | 2/1999 | Fodor et al. | 435/6 |
| 5,925,525 * | 7/1999 | Fodor et al. | 435/6 |
| 5,961,923 * | 10/1999 | Nova et al. | 422/68 |
| 5,974,164 * | 10/1999 | Chee | 382/129 |
| 6,040,138 * | 3/2000 | Lockhart et al. | 435/6 |

FOREIGN PATENT DOCUMENTS

| | | | |
|---|---|---|---|
| 0 307 476 | 3/1989 | (EP) | G06K/9/00 |
| 0 235 726 | 5/1989 | (EP) | G06K/9/00 |
| 0 392 546 | 10/1990 | (EP) | G07K/9/00 |
| 0 717 113 | 7/1996 | (EP) | G06K/9/00 |
| 0 848 067 | 6/1998 | (EP) | G06K/9/00 |

(List continued on next page.)

OTHER PUBLICATIONS

U.S. application No. 08/828,952, Webster et al., filed Mar. 28, 1997.

U.S. application No. 08/531,137, Chee et al., filed Oct. 16, 1995.

Drmanac, "Sequencing of Megabase Plus DNA by Hybridization: Theory of the Method", *Genomics*, 4:114–128 (1989).

(List continued on next page.)

*Primary Examiner*—Matthew C. Bella
*Assistant Examiner*—Choobin Mahmood
(74) *Attorney, Agent, or Firm*—Townsend and Townsend and Crew LLP

(57) ABSTRACT

System and method for organizing information relating to polymer probe array chips including oligonucleotide array chips. A database model is provided which organizes information relating to sample preparation, chip layout, application of samples to chips, scanning of chips, expression analysis of chip results, etc. The model is readily translatable into database languages such as SQL. The database model scales to permit mass processing of probe array chips.

14 Claims, 7 Drawing Sheets

FOREIGN PATENT DOCUMENTS

| | | | | |
|---|---|---|---|---|
| WO 89/11548 | 11/1989 | (WO) | ............................. | G06K/9/00 |
| WO 90/15070 | 12/1990 | (WO) | ............................. | G06K/9/00 |
| WO 92/10092 | 6/1992 | (WO) | ............................. | G06K/9/00 |
| WO 92/10588 | 6/1992 | (WO) | ............................. | G06K/9/00 |
| WO 93/22456 | 11/1993 | (WO) | ............................. | G06K/9/00 |
| WO 95/11995 | 5/1995 | (WO) | ............................. | G06K/9/00 |
| WO 96/23078 | 8/1996 | (WO) | ............................. | G06K/9/00 |
| WO 97/10365 | 3/1997 | (WO) | ............................. | G06K/9/00 |
| WO 97/17317 | 5/1997 | (WO) | ............................. | G06K/9/00 |
| WO 97/19410 | 5/1997 | (WO) | ............................. | G06K/9/00 |
| WO 97/27317 | 7/1997 | (WO) | ............................. | G06K/9/00 |
| WO 97/29212 | 8/1997 | (WO) | ............................. | G06K/9/00 |

OTHER PUBLICATIONS

Gibbs et al., "Detection of Single DNA Base Differences by Competitive Oligonucleotide Priming", *Nucleic Acid Res.*, 17(7):2437–2448 (1989).

Guatelli et al., "Isothermal, In Vitro Amplification of Nucleic Acids by a Multienzyme Reaction Modeled After Retroviral Replication", *Proc. Natl. Acad. Sci. USA*, 87(5):1874–1878 (1990).

Gusella, "DNA Polymorphism and Human Disease", *Annu. Rev. Biochem.*, 55:831–854 (1986).

IntelliGenetics Suite (TM), Release 5.4, Advanced Training Manual, Jan. 1993, published by IntelliGenetics, Inc., 700 East El Camino Real, Mountain View, California 94040, USA, pp. (1–6)—(1–19) and (2–9)—(2–14), see entire document.

Kwoh et al., "Transcription–Based Amplification System and Detection of Amplified Human Immunodeficiency Virus Type 1 With a Bead–Based Sandwich Hybridization Format", *Proc. Natl. Acad. Sci. USA*, 86(4):1173–1177 (1989).

Landegren et al., "A Ligase–Mediated Gene Detection Technique", *Science*, 241(4869):1077–1080 (1988).

Mattila et al., "Fidelity of DNA Synthesis by the *Thermococcus litorallis* DNA Polymerase—An Extremely Heat Stable Enzyme With Proofreading Activity", *Nucleic Acids Res.*, 19(18):4967–4973 (1991).

Okubo et al., "Large Scale cDNA Sequencing for Analysis of Quantitative and Qualitative Aspects of Gene Expression", *Nature Genetics*, 2(3):173–179 (1993).

Orita et al., "Detection of Polymorphisms of Human DNA by Gel Electrophoresis as Single–Strand Conformation Polymorphisms", *Proc. Natl. Acad. Sci. USA*, 86(8):2766–2770 (1989).

Saiki et al., "Analysis of Enzymatically Amplified Beta–Globin and HLA–DQ Alpha DNA with Allele–Specific Oligonucleotide Probes", *Nature*, 324(6093):163–166 (1986).

Wu et al., "The Ligation Amplification Reaction (LAR)—Amplification of Specific DNA Sequences Using Sequential Rounds of Template–Dependent Ligation", *Genomics*, 4(4):560–569 (1989).

Zhao et al., "High–density cDNA filter analysis: a novel approach for large–scale, quantitative analysis of gene expression," *Gene*, 156:207–213 (1995).

PR Newswire, "Gene Logic to Use Affymetrix GeneChip Arrays to Build Gene Expression Database Products", Jan. 11, 1999.

Adams et al., "Complementary DNA Sequencing: Expressed Sequence Tags and Human Genome Project", *Science*, 252(5013):1651–1656 (1991).

Frickett et al., "Development Of A Database For Nucleotide Sequences", *Mathematical Methods for DNA Sequences*, CRC Press, Ed. Waterman, pp. 2–34 (1989).

Hara et al., "Subtractive cDNA Cloning Using Oligo(dT)$_{30}$–Latex And PCR: Isolation Of cDNA Clones Specific To Undifferentiated Human Embryonal Carcinoma Cells", *Nucleic Acids Res.*, 19(25):7097–7104 (1991).

Khan et al., "Single Pass Sequencing And Physical And Genetic Mapping Of Human Brain cDNAs", *Nat Genet.*, 2(3):180–185 (1992).

Matsubara et al., "Identification Of New Genes By Systematic Analysis Of cDNAs And Database Construction", *Curr. Opin. Biotechnol.*, 4(6):672–677 (1993).

* cited by examiner

METHOD AND APPARATUS FOR PROVIDING A BIOINFORMATICS DATABASE

CROSS-REFERENCE TO RELATED APPLICATIONS

The present application claims priority from U.S. Prov. App. No. 60/053,842 filed Jul. 25, 1997, entitled COMPREHENSIVE BIO-INFORMATICS DATABASE, from U.S. Prov. App. No. 60/069,198 filed on Dec. 11, 1997, entitled COMPREHENSIVE DATABASE FOR BIOINFORMATICS, and from U.S. Prov. App. No. 60/069,436, entitled GENE EXPRESSION AND EVALUATION SYSTEM, filed on Dec. 11, 1997. The contents of all three provisional applications are herein incorporated by reference.

The subject matter of the present application is related to the subject matter of the following three co-assigned applications filed on the same day as the present application. GENE EXPRESSION AND EVALUATION SYSTEM, METHOD AND SYSTEM FOR PROVIDING A POLYMORPHISM DATABASE, METHOD AND SYSTEM FOR PROVIDING A PROBE ARRAY CHIP DESIGN DATABASE. The contents of these three applications are herein incorporated by reference.

BACKGROUND OF THE INVENTION

The present invention relates to the collection and storage of information pertaining to processing of biological samples.

Devices and computer systems for forming and using arrays of materials on a substrate are known. For example, PCT application WO92/10588, incorporated herein by reference for all purposes, describes techniques for sequencing or sequence checking nucleic acids and other materials. Arrays for performing these operations may be formed in arrays according to the methods of, for example, the pioneering techniques disclosed in U.S. Pat. No. 5,143,854 and U.S. Pat. No. 5,571,639, both incorporated herein by reference for all purposes.

According to one aspect of the techniques described therein, an array of nucleic acid probes is fabricated at known locations on a chip or substrate. A fluorescently labeled nucleic acid is then brought into contact with the chip and a scanner generates an image file indicating the locations where the labeled nucleic acids bound to the chip. Based upon the identities of the probes at these locations, it becomes possible to extract information such as the monomer sequence of DNA or RNA. Such systems have been used to form, for example, arrays of DNA that may be used to study and detect mutations relevant to cystic fibrosis, the P53 gene (relevant to certain cancers), HIV, and other genetic characteristics.

Computer-aided techniques for monitoring gene expression using such arrays of probes have also been developed as disclosed in EP Pub No. 0848067 and PCT publication No. WO 97/10365, the contents of which are herein incorporated by reference. Many disease states are characterized by differences in the expression levels of various genes either through changes in the copy number of the genetic DNA or through changes in levels of transcription (e.g., through control of initiation, provision of RNA precursors, RNA processing, etc.) of particular genes. For example, losses and gains of genetic material play an important role in malignant transformation and progression. Furthermore, changes in the expression (transcription) levels of particular genes (e.g., oncogenes or tumor suppressors), serve as signposts for the presence and progression of various cancers.

These computer-aided techniques for sequencing and expression monitoring are themselves multi-stage processes including, e.g., stages of selecting sequences, overall chip layout, mask design, probe synthesis, sample preparation, application of samples to chips, scanning of samples, and analysis of scanning results. For each stage, there is associated control information that determines in some way how the processing of the stage is performed. For many stages, there is also result information generated during the stage. Processing at one stage may depend on control information or result information from a previous stage. Thus, there is a need to organize all of the relevant information for convenient access and retrieval.

Many of the contemplated applications of probe array chips involve performing all of the various stages on a very large scale. For example, consider surveying a large population of human subjects to discover oncogenes and tumor suppressor genes relevant to a particular form of cancer. Large numbers of samples must be collected and processed. Information about the sample donors and sample preparation condition should be maintained to facilitate later analysis. The probe array chips will have associated layout information. Each chip will be processed with samples and scanned individually. Each chip will thus have its own scanning results. Finally, the scanning results will be interpreted and analyzed for many subjects in an effort to identify the oncogenes and tumor suppressors. The quantity of information to store and correlate is vast. Compounding the information management problem, equipment and other laboratory resources may be shared with other projects. A single laboratory may service many clients, each client in turn requesting completion of multiple projects. What is needed is a system and method suitable for storing and organizing large quantities of information used in conjunction with probe array chips.

SUMMARY OF THE INVENTION

The present invention provides system and method for organizing information relating to polymer probe array chips including oligonucleotide array chips. A database model is provided which organizes information relating to sample preparation, chip layout, application of samples to chips, scanning of chips, expression analysis of chip results, etc. The model is readily translatable into database languages such as SQL. The database model scales to permit mass processing of probe array chips.

According to a first aspect of the present invention, a computer-implemented method for managing information relating to processing of polymer probe arrays, includes a step of creating an electronically-stored experiment table. The experiment table lists for each of a plurality of experiments a first identifier identifying a target sample applied to an polymer probe array chip in a particular experiment, and a second identifier identifying the polymer probe array chip to which the target sample was applied in the particular experiment. The method further includes a step of creating an electronically-stored chip table. The chip table lists for each of a plurality of polymer probe array chips: the second identifier identifying a particular polymer probe array chip; and a third identifier specifying a layout of polymer probes on the oligonucleotide array chip.

According to a second aspect of the present invention, a computer-implemented method for managing information relating to processing of oligonucleotide arrays, includes a step of creating an electronically stored analysis table. The analysis table lists for each of a plurality of expression analysis operation a first identifier specifying a particular analysis operation and a second identifier specifying oligonucleotide array processing result information on which the particular expression analysis operation has been performed. The method further includes a step of creating an electronically stored gene expression result table. The gene expression result table lists for each of selected ones of the plurality of analysis operations, a list of genes and results of the particular expression analysis operation as applied to each of the genes.

According to a third aspect of the present invention, a computer-implemented method for managing information relating to processing of polymer probe arrays includes steps of: storing in an electronically-stored experiment table for each of a plurality of experiments, a first identifier identifying a target sample applied to an polymer probe array chip in a particular experiment; storing in the electronically-stored experiment table for each of the plurality of experiments a second identifier identifying the polymer probe array chip to which the target sample was applied in the particular experiment; storing in an electronically-stored chip table for each of a plurality of polymer probe array chips, the second identifier identifying a particular polymer probe array chip; and storing in the electronically-stored chip table for each of the plurality of polymer probe chips a third identifier specifying a layout of polymer probes on the polymer probe array chip.

A further understanding of the nature and advantages of the inventions herein may be realized by reference to the remaining portions of the specification and the attached drawings.

DESCRIPTION OF SPECIFIC EMBODIMENTS

Biological Material Analysis System

One embodiment of the present invention operates in the context of a system for analyzing biological or other materials using arrays that themselves include probes that may be made of biological materials such as RNA or DNA. The VLSIPS™ and GeneChip™ technologies provide methods of making and using very large arrays of polymers, such as nucleic acids, on very small chips. See U.S. Pat. No. 5,143,854 and PCT Patent Publication Nos. WO 90/15070 and 92/10092, each of which is hereby incorporated by reference for all purposes. Nucleic acid probes on the chip are used to detect complementary nucleic acid sequences in a sample nucleic acid of interest (the "target" nucleic acid).

It should be understood that the probes need not be nucleic acid probes but may also be other polymers such as peptides. Peptide probes may be used to detect the concentration of peptides, polypeptides, or polymers in a sample. The probes must be carefully selected to have bonding affinity to the compound whose concentration they are to be used to measure.

Figure 1:
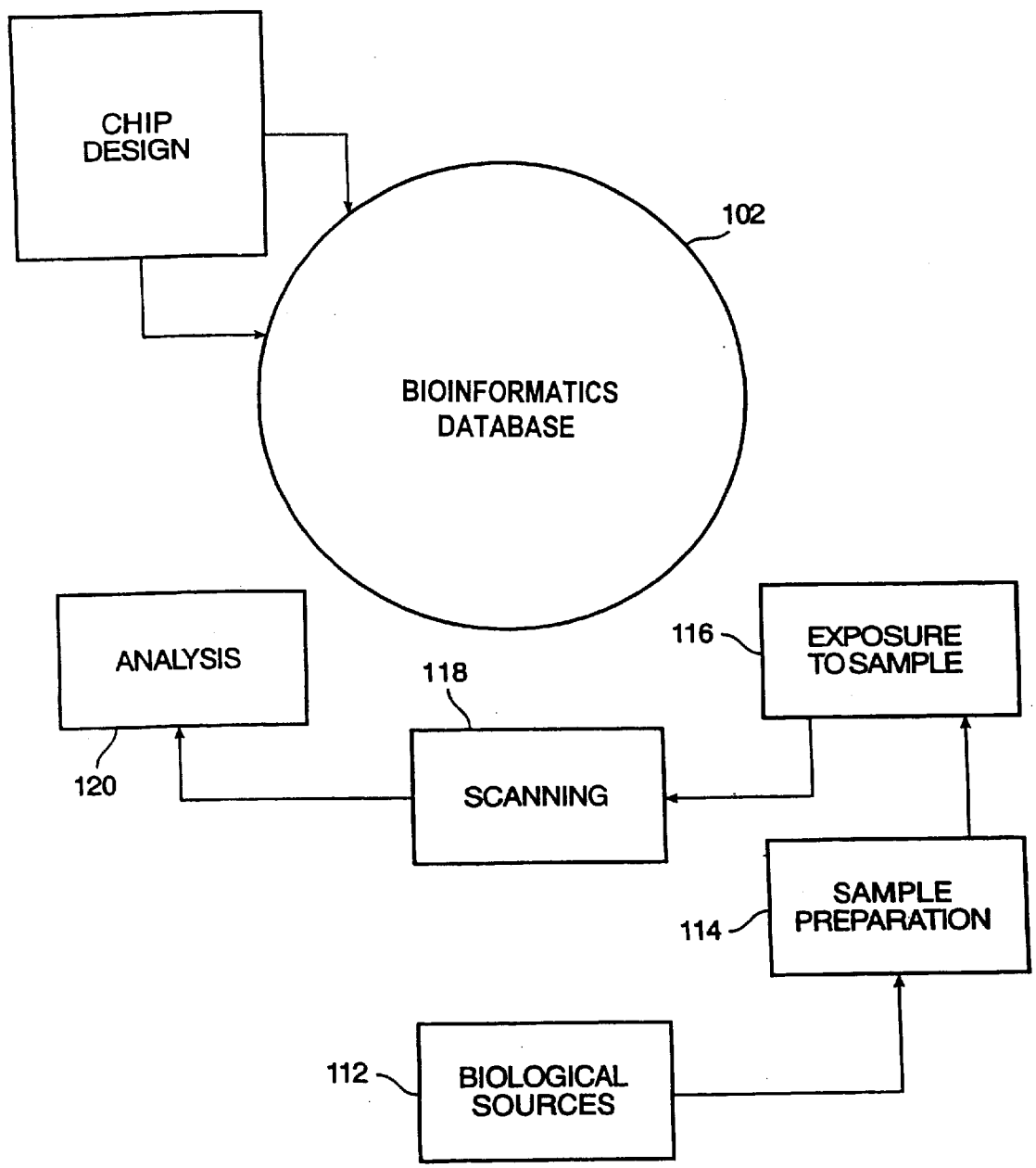
FIG. 1 illustrates an overall system and process for forming and analyzing arrays of biological materials such as DNA or RNA.

FIG. 1 illustrates an overall system 100 for forming and analyzing arrays of biological materials such as RNA or DNA. At the center of system 100 is a bioinformatics database 102. Bioinformatics database 102 maintains information relevant to the various stages of forming and processing the arrays as well as to interpreting and analyzing the results. Bioinformatics database 102 facilitates large scale processing of arrays.

A chip design system 104 is used to design arrays of polymers such as biological polymers such as RNA or DNA. Chip design system 104 may be, for example, an appropriately programmed Sun Workstation or personal computer or workstation, such as an IBM PC equivalent, including appropriate memory and a CPU. Chip design system 104 obtains inputs from a user regarding chip design objectives including characteristics of genes of interest, and other inputs regarding the desired features of the array. Optionally, chip design system 104 may obtain information regarding a specific genetic sequence of interest from bioinformatics database 102 or from external databases such as GenBank. The output of chip design system 104 is a set of chip design computer files in the form of, for example, a switch matrix, as described in PCT application WO 92/10092, and other associated computer files. The chip design computer files form a part of bioinformatics database 102. Systems for designing chips for sequence determination and expression analysis are disclosed in U.S. Pat. No. 5,571,639 and in PCT application WO 97/10365, the contents of which are herein incorporated by reference.

The chip design files are input to a mask design system (not shown) that designs the lithographic masks used in the fabrication of arrays of molecules such as DNA. The mask design system designs the lithographic masks used in the fabrication of probe arrays. The mask design system generates mask design files that are then used by a mask construction system (not shown) to construct masks or other synthesis patterns such as chrome-on-glass masks for use in the fabrication of polymer arrays.

The masks are used in a synthesis system (not shown). The synthesis system includes the necessary hardware and software used to fabricate arrays of polymers on a substrate or chip. The synthesis system includes a light source and a chemical flow cell on which the substrate or chip is placed. A mask is placed between the light source and the substrate/chip, and the two are translated relative to each other at appropriate times for deprotection of selected regions of the chip. Selected chemical reagents are directed through the flow cell for coupling to deprotected regions, as well as for washing and other operations. The substrates fabricated by the synthesis system are optionally diced into smaller chips. The output of the synthesis system is a chip ready for application of a target sample.

Information about the mask design, mask construction, and probe array synthesis systems is presented by way of background. Bioinformatics database 102 may or may not include information related to their operation.

A biological source 112 is, for example, tissue from a plant or animal. Various processing steps are applied to material from biological source 112 by a sample preparation system 114. These steps may include isolation of mRNA, precipitation of the mRNA to increase concentration, etc, synthesis of cDNA from mRNA. The result of the various processing steps is a target sample ready for application to the chips produced by the synthesis system 110. Sample preparation methods for expression analysis are discussed in detail in WO97/10365.

The prepared samples include monomer nucleotide sequences such as RNA or DNA. When the sample is applied to the chip by a sample exposure system 116, the nucleotides may or may not bond to the probes. The nucleotides have been tagged with fluoroscein labels to determine which probes have bonded to nucleotide sequences from the sample. The prepared samples will be placed in a scanning system 118. Scanning system 118 includes a detection device such as a confocal microscope or CCD (charge-coupled device) that is used to detect the location where labeled receptors have bound to the substrate. The output of scanning system 118 is an image file(s) indicating, in the case of fluorescein labeled receptor, the fluorescence intensity (photon counts or other related measurements, such as voltage) as a function of position on the substrate. These image files also form a part of bioinformatics database 102. Since higher photon counts will be observed where the labeled receptor has bound more strongly to the array of polymers, and since the monomer sequence of the polymers on the substrate is known as a function of position, it becomes possible to determine the sequence(s) of polymer (s) on the substrate that are complementary to the receptor.

The image files and the design of the chips are input to an analysis system 120 that, e.g., calls base sequences, or determines expression levels of genes or expressed sequence tags. The expression level of a gene or EST is herein understood to be the concentration within a sample of mRNA or protein that would result from the transcription of the gene or EST. Such analysis techniques are disclosed in WO97/10365 and U.S. application Ser. No. 08/531,137, the contents of which are herein incorporated by reference. Analysis results are stored in bioinformatics database 102.

Chip design system 104, analysis system 120 and control portions of exposure system 116, sample preparation system 114, and scanning system 118 may be appropriately programmed computers such as a Sun workstation or IBM-compatible PC. An independent computer for each system may perform the computer-implemented functions of these systems or one computer may combine the computerized functions of two or more systems. One or more computers may maintain bioinformatics database 102 independent of the computers operating the systems of FIG. 1 or database 102 may be fully or partially maintained by these computers.

Figure 2A:
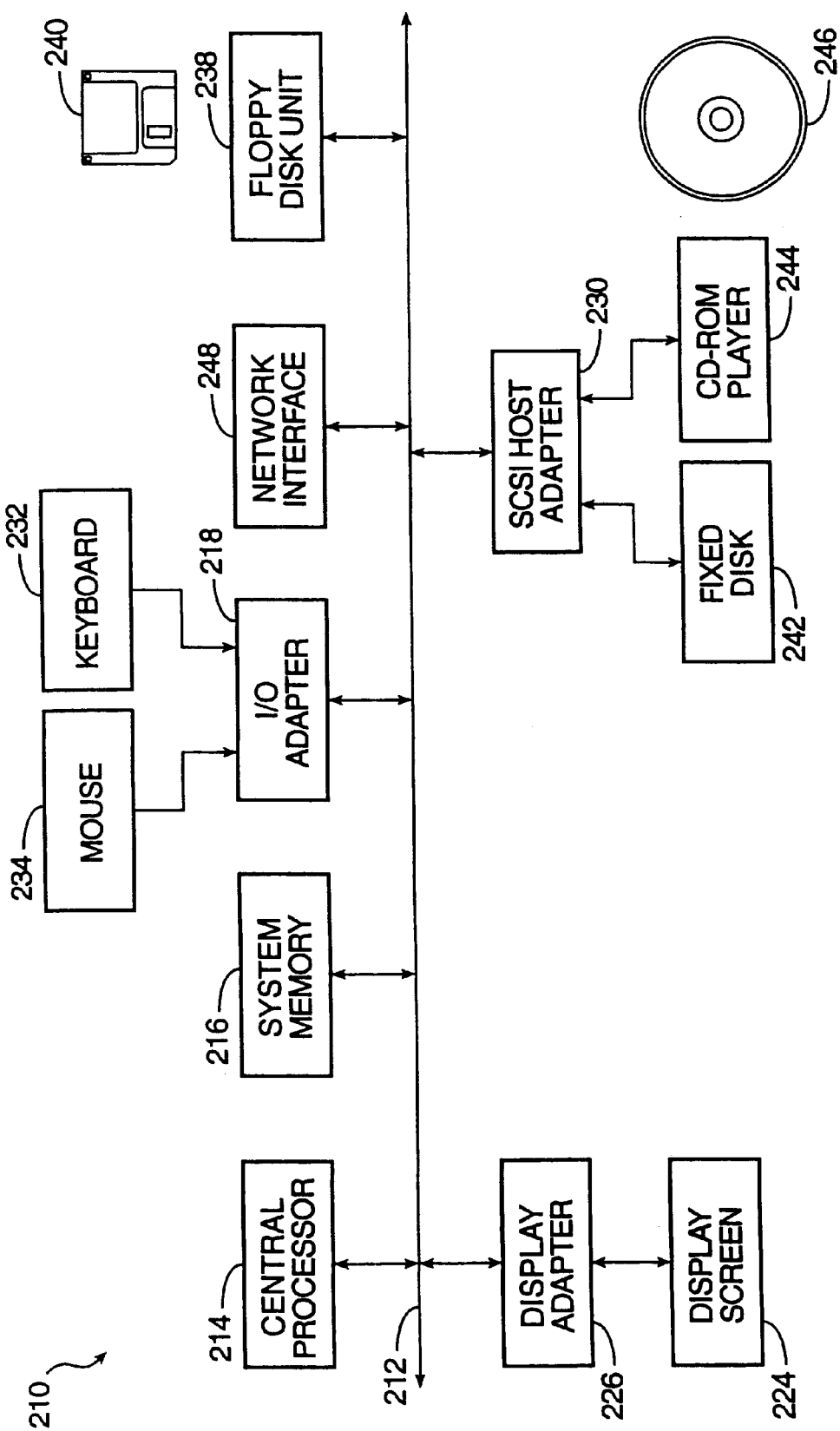
FIG. 2A illustrates a computer system suitable for use in conjunction with the overall system of FIG. 1.

FIG. 2A depicts a block diagram of a host computer system 10 suitable for implementing the present invention. Host computer system 210 includes a bus 212 which interconnects major subsystems such as a central processor 214, a system memory 216 (typically RAM), an input/output (I/O) adapter 218, an external device such as a display screen 224 via a display adapter 226, a keyboard 232 and a mouse 234 via an I/O adapter 218, a SCSI host adapter 236, and a floppy disk drive 238 operative to receive a floppy disk 240. SCSI host adapter 236 may act as a storage interface to a fixed disk drive 242 or a CD-ROM player 244 operative to receive a CD-ROM 246. Fixed disk 244 may be a part of host computer system 210 or may be separate and accessed through other interface systems. A network interface 248 may provide a direct connection to a remote server via a telephone link or to the Internet. Network interface 248 may also connect to a local area network (LAN) or other network interconnecting many computer systems. Many other devices or subsystems (not shown) may be connected in a similar manner.

Also, it is not necessary for all of the devices shown in FIG. 2A to be present to practice the present invention, as discussed below. The devices and subsystems may be interconnected in different ways from that shown in FIG. 2A. The operation of a computer system such as that shown in FIG. 2A is readily known in the art and is not discussed in detail in this application. Code to implement the present invention, may be operably disposed or stored in computer-readable storage media such as system memory 216, fixed disk 242, CD-ROM 246, or floppy disk 240.

Figure 2B:
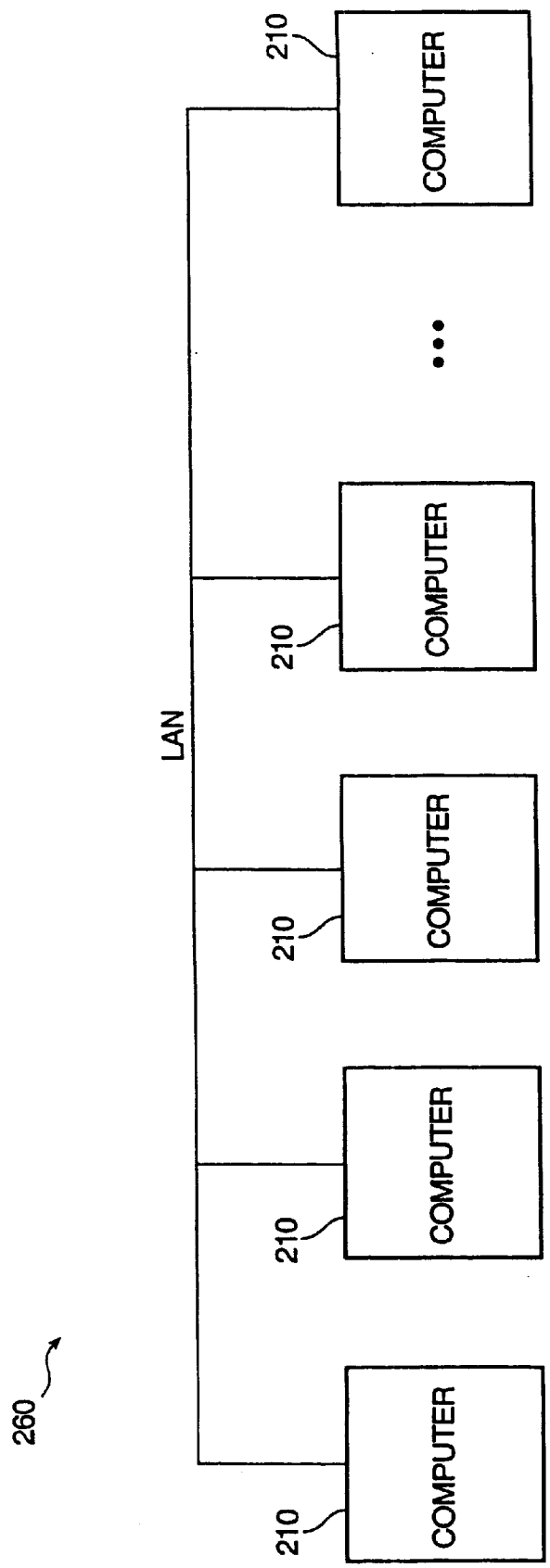
FIG. 2B illustrates a computer network suitable for use in conjunction with the overall system of FIG. 1.

FIG. 2B depicts a network 260 interconnecting multiple computer systems 210. Network 260 may be a local area network (LAN), wide area network (WAN), etc. Bioinformatics database 102 and the computer-related operations of the other elements of FIG. 2B may be divided amongst computer systems 210 in any way with network 260 being used to communicate information among the various computers. Portable storage media such as floppy disks may be used to carry information between computers instead of network 260.

Database General Model

Bioinformatics database 102 is preferably a relational database with a complex internal structure. The structure and contents of bioinformatics database 102 will be described with reference to a logical model that describes the contents of tables of the database as well as interrelationships among the tables. A visual depiction of this model will be an Entity Relationship Diagram (ERD) which includes entities, relationships, and attributes. A detailed discussion of ERDs is found in "ERwin version 3.0 Methods Guide" available from Logic Works, Inc. of Princeton, N.J., the contents of which are herein incorporated by reference. Those of skill in the art will appreciate that automated tools such as Developer 2000 available from Oracle will convert the ERD from FIG. 4 directly into executable code such as SQL code for creating and operating the database.

Figure 3:
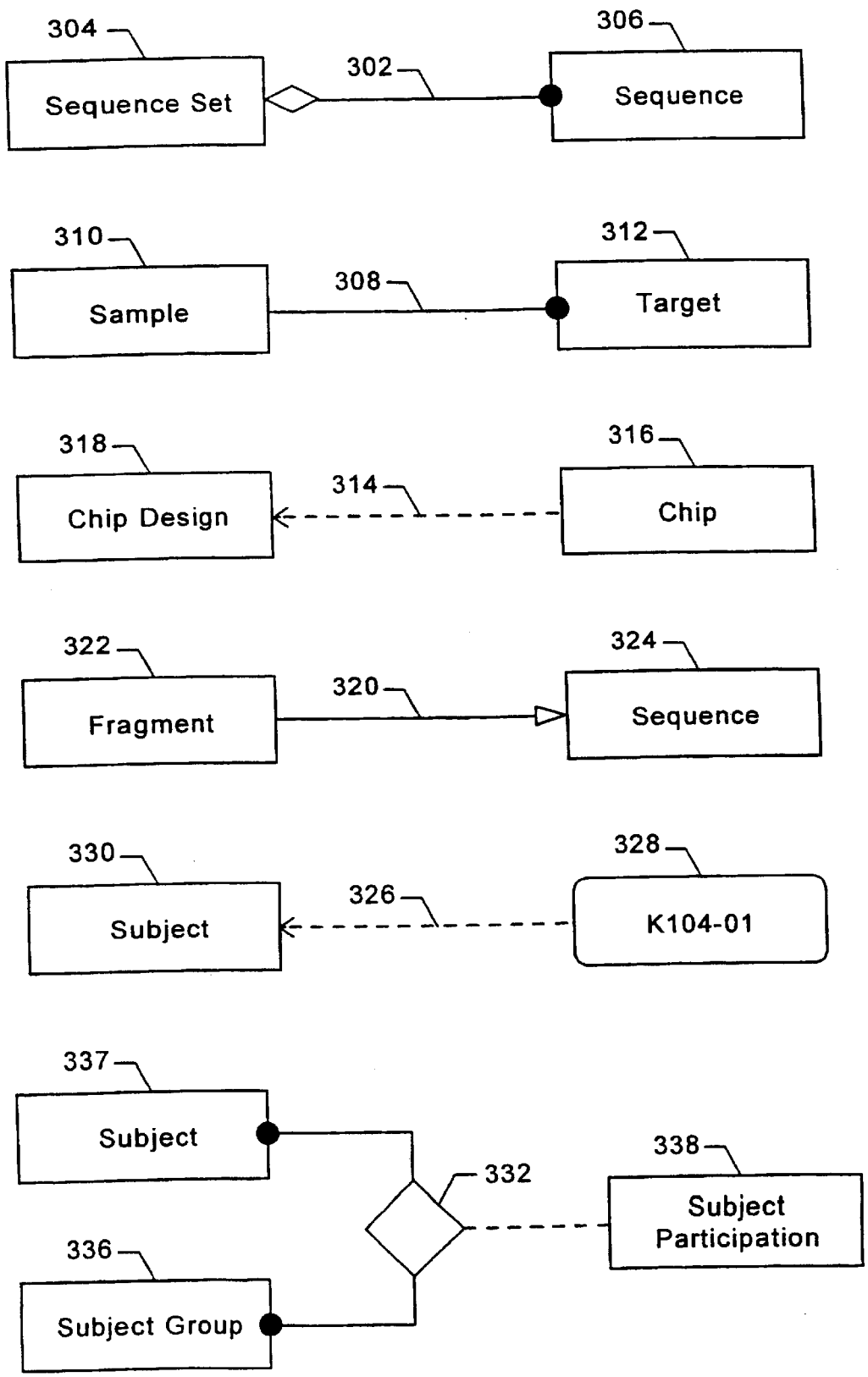
FIG. 3 illustrates a key for interpreting a database model.

FIG. 3 is a key to the ERD that will be used to describe the contents of bioinformatics database 102. An aggregation (or "has a") relationship 302 signifies that one entity has another entity. In the depicted example, a sequence set 304 has a sequence 306. A one to many association (or "classification") relationship 308 signifies that one entity defines an equivalence class of other entities. In the depicted example, a sample 310 defines an equivalence class of targets 312. A MetaClass relationship 314 signifies that a collection of one entity corresponds to another entity. In the depicted example, a collection of chips 316 corresponds to a chip design 318. A specialization (or "is a") relationship 320 indicates that one entity is another entity. In the depicted example, a fragment 322 is a sequence 324.

An instantiation relationship 326 signifies that one entity is an instance of a set of another entity. In the depicted example, K104-101 328 is an instance of the set of subjects 330. If instantiation leads to a set rather than a unique element, the set being instantiated is referred to as a metaclass. An associative object relationship 332 signifies that a subset of the cartesian product of a first set of entities and a second set of entities corresponds to a third set of entities. In the depicted example, a subject 334 participates in one or more subject groups 336 and each such subject participation 338 is an entity.

Figure 4A:
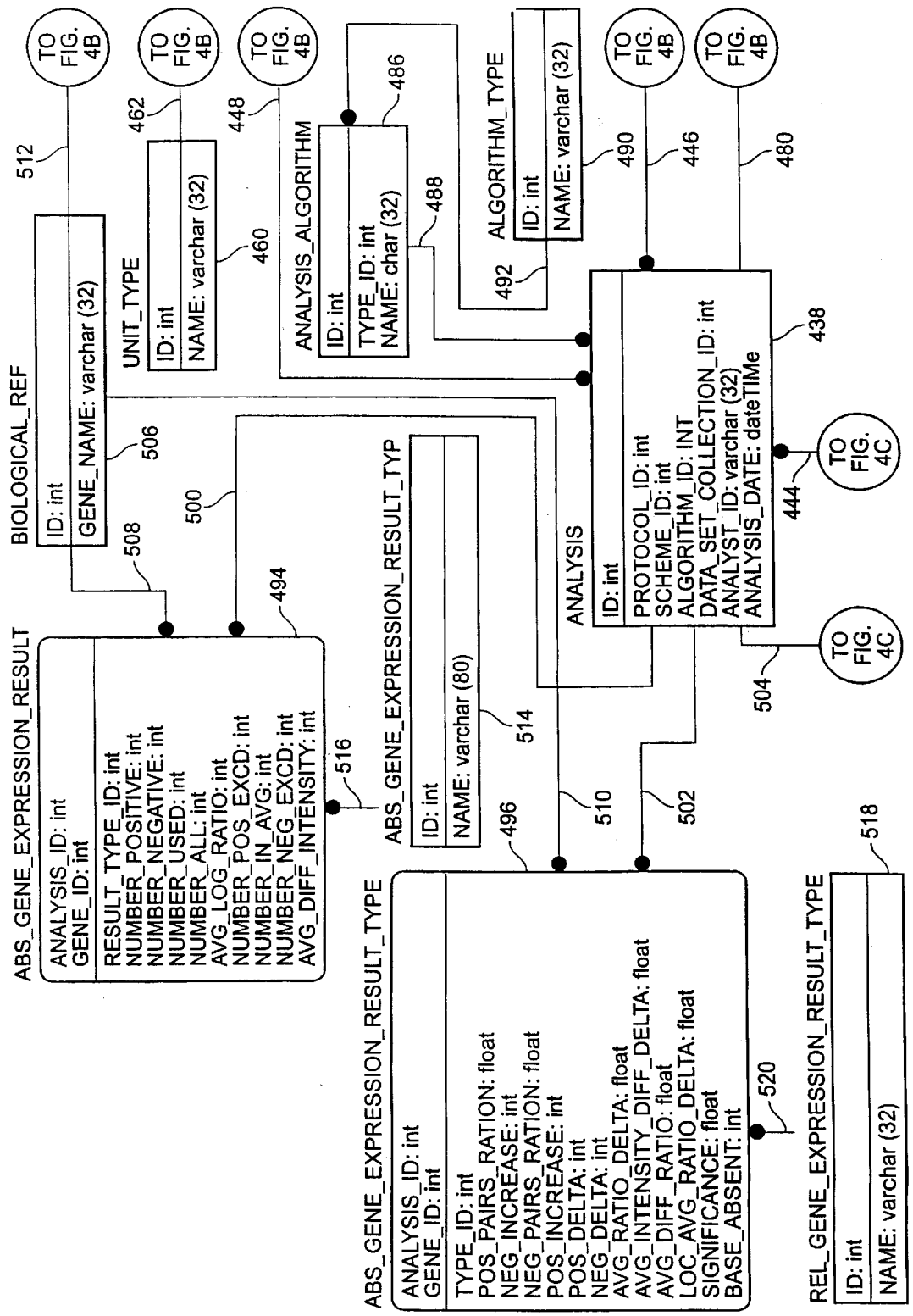
FIG. 4 illustrates a database model for maintaining information for the system and process of FIG. 1 according to one embodiment of the present invention.
Figure 4B:
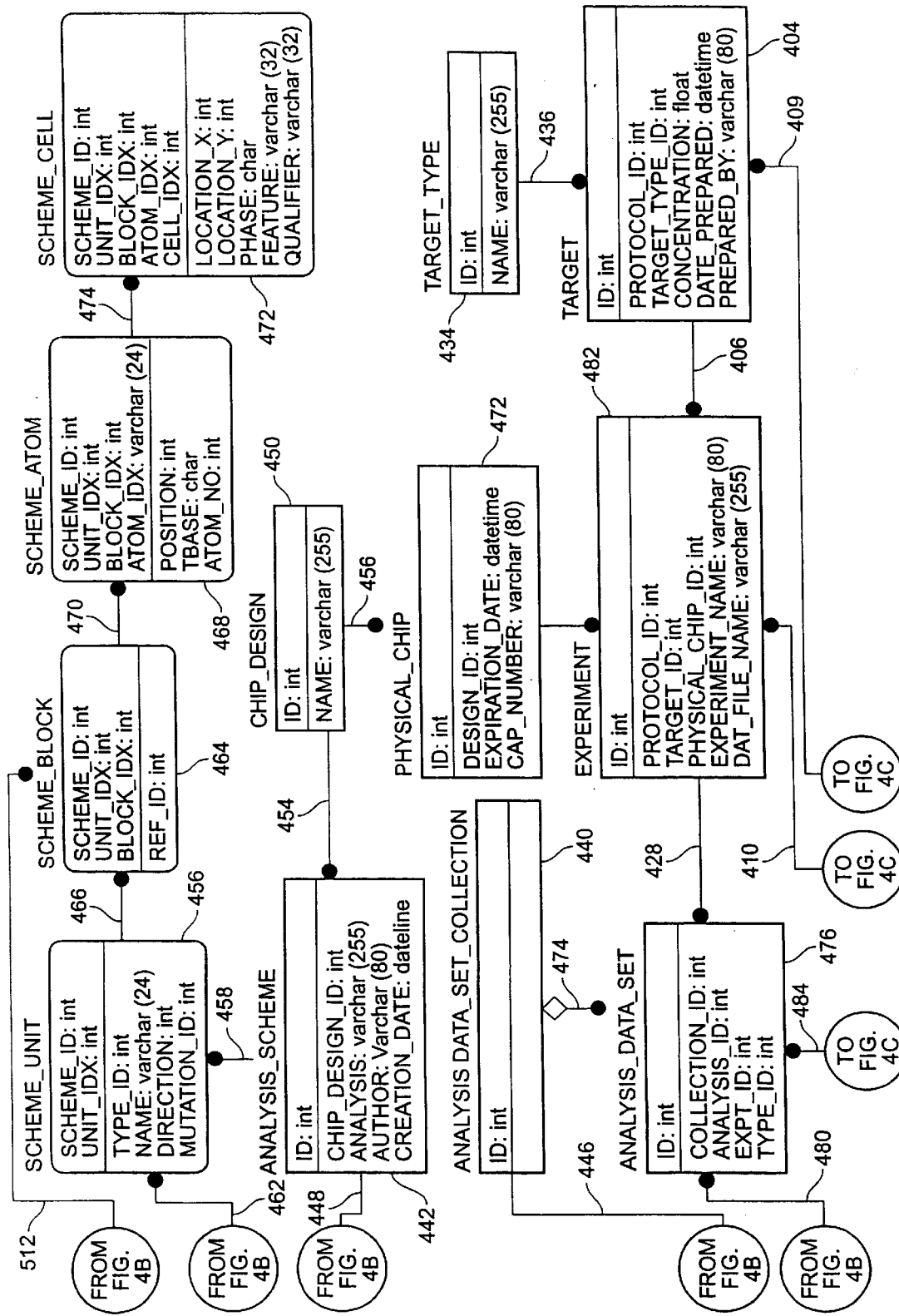
Figure 4C:
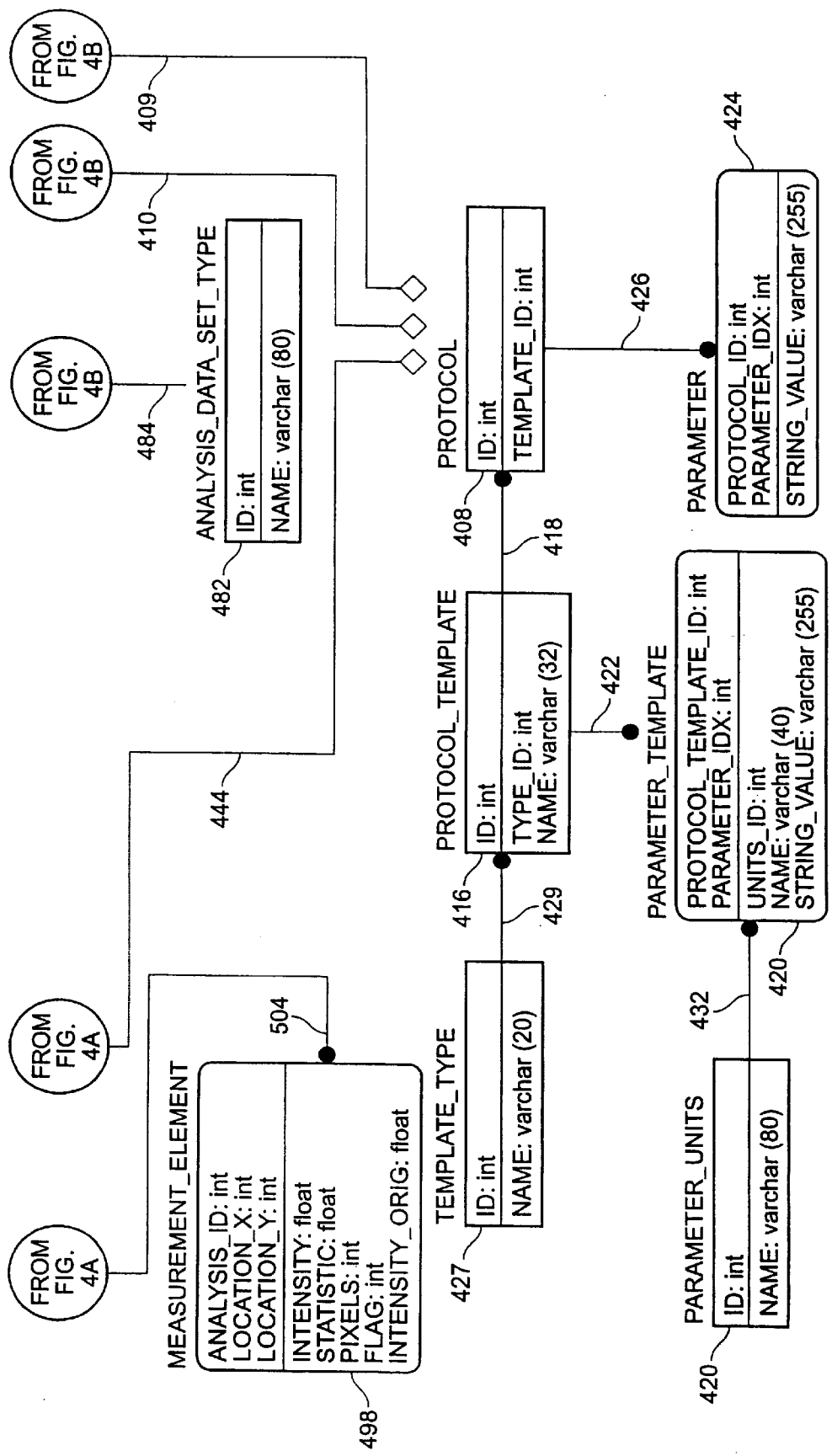

FIG. 4 is an entity relationship diagram (ERD) showing elements of bioinformatics database 102 according to one embodiment of the present invention.

Each rectangle in the diagram corresponds to a table in database 102. For each rectangle, the title of the table is listed above the rectangle. Within each rectangle, columns of the table are listed. Above a horizontal line within each rectangle are listed key columns, columns whose contents are used to identify individual records in the table. Below this horizontal line are the names of non-key columns. The lines between the rectangles identify the relationships between records of one table and records of another table. First, the relationships among the various tables will be described. Then, the contents of each table will be discussed in detail.

Certain details of bioinformatics database 102 pertain to expression analysis, although other types of analysis such as base calling and the discovery of polymorphisms may also be facilitated according to the present invention.

An experiment table 402 lists experiments performed on a target using a particular physical chip and is done according to a protocol. Targets are listed in a target table 404 linked to experiment table 402 by a one to many association relationship 406. Protocols are listed in a protocol table 408 linked to experiment table 402 by an aggregation relationship 410. Physical chips are listed in a physical chip table 412 linked to experiment table 402 by a one to many association relationship 414. Thus, each record in experiment table 402 is linked to a record from protocol table 408, and to a record from physical chip table 412, and from the target table associated with it. Also, each record in target table 404 is linked to a record in protocol table 408. Thus, there is also an aggregation relationship 409 between protocol table 408 and target table 404. Although not depicted in this way, an experiment is an associative object or defines an associative relationship between physical chip, target, and protocol.

A protocol is generally a description of the parameters used to control a procedure such as an experiment or preparation of a target. The protocol used for an experiment includes quantities that are important to preserve for later use such as temperature, identification of instruments, etc.

A protocol table itself does not have any specific information associated with it. A protocol is based on a protocol template. A protocol template has many associated parameter templates. Thus, there is a protocol template table 416 linked to protocol table 408 by a one to many association relationship 418 and to parameter template table 420 by a one to many association relationship 422. Each parameter template in parameter template table 420 lists parameters deemed to be important in a particular context such an experiment. The parameter templates may also include default values for particular parameters. Typically, a single record in protocol table 408 will be associated with a single record in protocol template table 416 which will in turn have multiple parameter templates in parameter template table 420 associated with it.

The parameters themselves are listed in a parameter table 424 to which protocol table 408 is linked by a one to many relationship 426. If when a protocol is actually used one or more default values identified in a parameter template get changed; those changes are recorded in a parameter table 424.

A template type associated with each protocol template indicates the kind of template. The template type identifies, for example, whether the template identifies parameters for experiments, for analysis, or for target preparation. Thus, a template type table 427 has a one to many association relationship 429 to protocol template table 416.

For each parameter listed in parameter template table 420, there is a unit of measurement for that parameter. Thus, a parameter units table 430 has a one to many relationship 432 to parameter template table 420.

For each target record in a target table 404 there is a target type record in a target type table 434. The target type records identifies a type of target source, such as blood, saliva, etc. There is a one to many association relationship 436 between target table 404 and target type table 434.

An analysis is carried out on an analysis data set collection according to a protocol and according to an analysis scheme. Thus, there is an analysis table 438, an analysis data set collection table 440, an analysis scheme table 442. There is an aggregation relationship 444 between protocol table 408 and analysis table 438, a one to many association relationship 446 between analysis data sent collection table 440 and analysis table 438, and an aggregation relationship 448 between analysis scheme table 442 and analysis table 438. A protocol for analysis is analogous to the protocols used for experiments and target preparation.

An analysis scheme record gives the logical layout of a chip type. A logical layout consists of a hierarchical assembly of units, blocks, atoms, and cells, each of which is detailed in a separate table. There may be more than one logical layout for a particular physical chip design because the same collection of probes of a single physical chip design may be usable for disparate analysis objectives.

There is a chip design table 450 that has a one to many association relationship 452 to physical chip table 412. The records of chip design table 450 identify a physical chip layout. There is also a one to many association relationship 454 between chip design table 450 and analysis scheme 442 to represent the possibility of multiple logical layouts for a particular physical layout.

A scheme unit table 456 lists records for units of the logical layout. A unit is a collection of probes that interrogate one or more biological items such as genes. There is a one to many relationship 458 between analysis scheme table 442 and scheme unit table 456. Each unit has an associated unit type listed in a unit type table 460 with a one to many association relationship 462 existing between unit type table 460 and scheme unit table 456.

A scheme block table 464 lists records for blocks of the logical layout. Although a one to many associative relationship 466 exists between scheme unit table 456 and scheme block table 464, there is only one block per unit in a preferred embodiment optimized for expression analysis. Each record of scheme block table 464 pertains to the probes used to evaluate a particular gene.

A scheme atom table 468 lists atoms of the logical layout. There is a one to many associative relationship 470 between scheme block table 464 and scheme atom table 468. Each atom corresponds to a combination of perfect match probe and mismatch probe.

A scheme cell table 472 lists cells of the logical layout. There is a one to many relationship 474 between scheme atom table 468 and scheme cell table 474. Each record of scheme cell table 472 gives information about a particular probe such as its location and how it relates to particular genes of interest.

An analysis data set collection identifies data to be analyzed. Each analysis data set collection includes one or more analysis data sets. An analysis data set may include data obtained either from an experiment or from a previously performed analysis. So, an analysis can be based on experiments to produce analysis results. Future analyses can be based on previous analyses to produce analysis results. Analysis data set collection table 440 has an aggregation relationship 474 to an analysis data set table 476. Experiment table 402 is linked to analysis data set table 476 by a one to many association relationship 478 as one possible source analysis data. Similarly analysis table 438 is linked to analysis data set table 476 by another one to many association relationship 480 as another possible source of data. Thus, there is effectively a loop between analysis table 438, analysis data set collection table 440, and analysis data set table 476 which defines a recursive relationship which makes it possible to define analyses based on previous analyses.

An analysis data set type table 482 for the analysis data sets listed in table 476. There is one type for data resulting from experiments and one type for data resulting from previous analysis. There is a many to one association relationship 484 between analysis data set table 476 and analysis data set type table 482.

An analysis listed in analysis table 438 has an associated analysis algorithm. Analysis algorithms are listed in an analysis algorithm table 486 linked to analysis table 438 by a one to many association relationship 488. In a preferred embodiment tailored to expression analysis, there may be three possible types of algorithm corresponding to: 1) analysis for a particular cell, 2) relative expression calling, and 3) absolute expression calling. An algorithm type table 490 is linked to analysis algorithm table 486 by a one to many association relationship 492.

Preferably, there are three result tables, an absolute gene expression result table 494, a relative gene expression result table 496, and a measurement element table 498. Each analysis may produce one or more absolute gene expression results, relative gene expression results, or measurement element results. Thus, there are one to many association relationships 500, 502, and 504 linking analysis table 438 to absolute gene expression table 494, relative gene expression table 496, and measurement element table 498 respectively.

A biological reference table 506 lists gene names. Each record in absolute gene expression result table 494 and relative gene expression result table 496 corresponds to a particular gene. Accordingly, there is a one to many associative relationship 508 between biological reference table 506 and absolute gene expression result table 494 and another such relationship 510 between biological reference table 506 and relative gene expression result table 416. There is also a one to many associative relationship 512 between biological reference table 406 and scheme block table 464 because each listed block corresponds to a particular named gene.

An absolute gene expression result type table 514 lists the types of absolute gene expression results including present, marginal, absent, and unknown. There is a one to many relationship 516 between absolute gene expression result type table 514 and absolute gene expression result table 494. A relative gene expression result table 518 lists the types of relative gene expression results including increased, no change, decreased, and unknown. There is a one to many relationship 520 between relative gene expression result type table 518 and relative gene expression result table 496.

Database Contents

The contents of the tables introduced above will now be presented in greater detail. It is to be understood that each table includes multiple records with each record having multiple fields corresponding to columns of the table. Experiment table 402 includes one record for each experiment run. An ID column is the primary key for experiment table 402 holding a unique identifier for each experiment. In describing the other tables, it will be understood that the "primary key" always serves this purpose. A protocol ID column identifies the protocol used for the experiment as listed in protocol table 408. A target ID column identifies the target sample used in the experiment as listed in target table 404. A physical chip ID column identifies the physical chip used in the experiment as listed in physical chip table 412. An experiment name column lists a unique name for each experiment. A DAT_FILE_NAME field lists a path name for a file storing results of the experiment on disk. This file will typically include pixel intensities recorded by scanning system 118.

Target type table 404 includes an ID column holding the primary key for the table. A protocol ID column identifies the protocol used in target sample preparation. A target type column gives the target type for the target sample as listed in target type table 434. A concentration column lists the concentration for each target sample. A date prepared column gives the date the target was prepared. A prepared by column identifies the name of the preparer of each target.

Target type table 434 lists the various target types such as blood, saliva, etc. There is an ID column holding the primary key for the table and a name column listing the names of the target types.

Physical chip table 412 lists the physical chips to which targets have been or may be applied. There is a primary key column. There is a design ID column which identifies the physical chip layout as listed in chip design field 450. There is an expiration date column listing the expiration dates of the chips and a cap number column identifying lot numbers for each chip.

Analysis table 438 includes one record for each analysis run. There is a primary key column for the table. There is a protocol ID column which identifies the protocol used for the analysis run as stored in protocol table 408. There is a scheme ID column which identifies the logical chip layout used for the analysis as listed in analysis scheme table 442. There is an algorithm ID column identifying the algorithm used in the analysis as listed in analysis algorithm table 486. A data set collection ID column identifies the data set collection used as input the analysis as listed in analysis data set collection table 440. An analyst ID column shows the name of the analyst for each analysis. An analysis date column gives the date of the analysis. A name column gives a unique name for the analysis.

Analysis data set collection table 440 lists data set collections upon which an analysis may be run. Table 440 includes a primary key column only.

Analysis data set table 476 lists data for analysis. There is a primary key column. There is a collection ID column which identifies which data set collection each data set belongs to as listed in analysis data set collection table 440. An analysis ID column identifies the analysis used to produce the data set, if the data set is in fact the product of an analysis. An experiment ID column identifies the experiment used to produce the data set, if the data set is instead the product of an experiment. A type ID column indicates whether the data set is the product of an experiment or an analysis.

Analysis data set type table 482 lists the types of analysis data sets, preferably "experiment" and "analysis" to indicate the data source. There is a primary key column and a name column giving the type name.

Analysis algorithm table 486 lists algorithms used for analysis. There is a primary key column and a name column giving an algorithm name. A type column indicates whether the algorithm produces absolute gene expression results, relative gene expression results, or results for a particular cell on the chip.

Algorithm type table 490 lists the types of algorithm results. There is a primary key column and a type column listing the different result types used in the type column of analysis algorithm table 486.

Measurement element table 498 lists analysis results for individual cells or probes. There is an analysis ID column identifying the analysis listed in analysis table 438 that produces the results listed in measurement elements table 498. There are location X and location Y columns giving the probe coordinates on the chip. The analysis ID, location X, and location Y columns are together a key for measurement element table 498. There is an intensity column which holds a calculated average fluorescent intensity for each cell or probe. A statistic column gives a standard deviation corresponding to the standard deviation of intensity measured over the probes. A pixels column lists the number of pixels used to compute the average intensities in the intensity column. A flag column stores a three bit flag for each individual cell analysis result. The first bit is set if the cell has been masked out of the analysis indicated in the analysis ID column and that the intensity and statistic columns therefore hold inapplicable data. A second bit indicates whether the analysis has determined the cell to be an outlier with results inconsistent with other cells. A third bit indicates if the cell intensity has modified compared to the value based on experimental measurements. An original intensity column lists the cell intensity if it has been modified, otherwise the entry in this column is set to "1."

Absolute gene expression result table 494 holds results from an absolute gene expression analysis with one record for each gene whose expression is measured by the chip. A typical expression analysis involves providing on the chip pairs of perfect match and mismatch probes. The perfect match probes hybridize perfectly with nucleotide sequences indicating expression of a particular gene. Each mismatch probe of a pair differs from its perfect match companion in one nucleotide position. An absolute gene expression analysis will typically indicate a probe pair to be positive or negative for expression of the particular gene based on ratio and/or difference thresholds.

An analysis ID column identifies the analysis as listed in analysis table 438 that produced the absolute gene expression results. An item ID column identifies the gene as listed in biological reference table 506 for which results are stored. The analysis ID and item ID together constitute a primary key for absolute gene expression result table 494. A result type ID column indicates whether the listed expression results indicate that the gene is present, marginal, absent, or unknown by referring to entries in absolute gene expression result type table 514. A number_positive column lists the number of probe pairs evaluated as positive. A number_negative column lists the number of probe pairs evaluated as negative. A number_used column indicates the number of probe pairs used in the analysis. A number_all column indicates the number of probes on the chip allocated for evaluating expression of the gene identified in the item ID column. An average log ratio column indicates the average logarithmic intensity ratio of perfect match to mismatch for all analyzed probe pairs. A number_positive_exceeds column indicates the difference between the number of positive probe pairs and the number of negative probe pairs. A number_negative_exceeds column indicates the excess of the number of negative probe pairs over the number of positive probe pairs. An average differential intensity column indicates the average difference in intensity between perfect match and mismatch probes for each pair. A number_in average column indicates the number of probe pairs used in computing the average.

Absolute gene expression result type table 518 lists the types present, marginal, absent, and unknown referred to by the result type column of absolute gene expression result table 494. There is a primary key column and a column for the names of the types.

Relative gene expression result table 496 holds results from comparative gene expression analyses. A comparative analysis is based on experiment results obtained from experiments on two targets: a baseline target and an experimental target. For example, the baseline target may be made from normal tissue while the experimental target may be made from cancerous tissue. Other tissue types used as targets may correspond to different stages of treatment or disease progression, different species, or different organs.

An analysis ID column identifies the analysis as listed in analysis table 438 that produced the relative gene expression results. An item ID column identifies the gene as listed in biological reference table 506 for which results are stored. The analysis ID and item ID together constitute a primary key for relative gene expression result table 496. A result type ID column indicates whether the listed relative expression results indicate increased expression, no change in expression, decreased expression, or an unknown change in expression by referring to entries in relative gene expression result type table 518. A positive pairs ratio column lists the ratio of the numbers of positive probe pairs between the two targets. A positive increase column indicates the number of probe pairs for which the difference between perfect match and mismatch hybridization intensities is significantly greater for the experimental target. A positive delta column indicates the difference between the number of positive probe pairs between the two targets. A negative pairs ratio column lists the ratio of the numbers of negative probe pairs for the two targets. A negative increase column indicates the number of probe pairs for which the difference between perfect match and mismatch hybridization intensities is significantly greater for the baseline target. A negative delta column indicates the difference between the number of negative probe pairs between the two targets. An average ratio delta column indicates the difference between average log ratios for the experimental and baseline targets. An average intensity difference delta column indicates the difference between the average intensity differences for the experimental and baseline targets. An average difference ratio column indicates the magnitude of the ratio of the average differences for the experimental and baseline targets. A log average ratio delta column indicates the difference between the log average ratios of the experimental and baseline targets. A significance columns provides an indication of the differences in expression between the experimental and baseline targets. This significance column is based on both the average difference ratio and the average intensity difference delta. A base absent column indicates whether the gene in question is seemingly not expressed in the baseline target. A difference call column (not shown) indicates whether the level of expression of the experimental target versus the baseline is increased, decreased, marginally increased, marginally decreased, or there is no detectable change in expression level.

Protocol table 408 associates parameters with experiments, target samples, and analyses. There is a primary key column and a column listing templates for protocols. Parameter table 424 stores all the captured parameters for experiments, target sample preparation, and analysis. There is a record for each parameter value. A protocol ID column identifies the protocol to which the parameter belongs. A parameter index column lists an index number for the parameter ranging from 1 to the number of parameters captured. The protocol ID and parameter index are together a key for protocol table 408. A string value column stores a value for the parameter.

Protocol template table 416 holds templates for protocols and associates the protocols listed in protocol table 408 with parameter sets listed by parameter template table 420. There is a primary key column. There is a template type column that identifies the type of template, e.g., for experiments, for analyses, for targets. There is a name column that lists a unique name for each protocol template.

Parameter template table 420 contains the parameter names and parameter default values associated with each protocol template. Each parameter has an associated record here. A protocol template ID column identifies the protocol template with which the parameter is associated. A parameter index column gives the index number for the parameter. Together the protocol template ID and parameter index are a key for parameter template table 420. A units ID column gives a unit of measurement for the parameter selected from ones listed in parameter units table 430. A name column gives the name of the parameter. A string value column gives the value of the parameter.

Template type table 427 lists the various types of protocol templates, e.g., templates for experiments, templates for analyses, templates for preparation of targets. There is a primary key column and a name column giving the type names.

Parameter units table 430 lists the various units of measurement used for parameters. There is a primary key column and a name column giving the unit name.

Chip design table 450 lists chip types. There is a primary key column and a name column giving unique names for each chip. Each chip type has a characteristic physical layout.

Analysis scheme table 442 lists logical layouts for chip types. A logical layout consists of a hierarchical assembly of units, blocks, atoms, and cells. There is a primary key column. A chip design ID column identifies the chip type for each logical layout. The same chip type may have more than one logical layout.

Unit type table 460 lists various types of units that make up a logical layout. There is a primary key column and a name column listing unique names for each unit type.

Scheme unit table 456 stores a record for each unit in the logical layout. There is a scheme ID column identifying the logical layout with which the unit is associated. There is a unit index column giving an index number for the unit ranging from 1 to the total number of units on the chip. The scheme ID column and unit index column together operate as a key to scheme unit table 456. There is a type ID column giving the unit type for each unit. A name column gives a name for each unit. A direction column indicates whether the unit interrogates in a coding or non-coding direction, i.e., whether the sample contains sequence from the sense DNA strand or the anti-sense DNA strand.

Scheme block table 464 stores a record for each block. Each block of the logical layout interrogates the activity of a single gene. There is a scheme ID column indicating the logical layout to which the block belongs. A unit index column indicates the unit to which the block belongs. A block index column gives an index number for the block, ranging from 1 to the number of blocks in the unit. The scheme ID, unit index, and block index together constitute a primary key for scheme block table 464. An item ID column identifies the interrogated gene by reference to biological reference table 506.

Scheme atom table 468 lists records for every atom of the logical layout. Atoms correspond to pairs of perfect match and mismatch probes. A scheme ID column identifies the logical layout to which the atom belongs. A unit index column indicates the unit to which the atom belongs. A block index column indicates the block to which the atom belongs. An atom index column gives an index number for the atom ranging from 1 to the number of atoms in the block. Together, the scheme ID, unit index, block index, and atom index constitute a key to scheme atom table 468. A position column indicates the sequence position in which the perfect match and mismatch probe differ. A T-base column indicates the base in the mismatch probe at the substitution position. An atom number column gives position information for the probe pair within its unit.

Scheme cell table 472 lists records for every cell of the logical layout. Cells correspond to individual probes. There are preferably two cells for each atom. A scheme ID column identifies the logical layout to which the cell belongs. A unit index column indicates the unit to which the cell belongs. A block index column indicates the block to which the cell belongs. An atom index column indicates the atom to which the cell belongs. A cell index identifies the cell within the atom. Together, the scheme ID, unit index, block index, atom index, and cell index constitute a key to scheme cell table 472. An x location column indicates an x coordinate for the cell on the chip. A y location column indicates a y coordinate for the cell on the chip. A probe base column identifies the probe base at the substitution position for the atom or probe pair. A feature column gives a string describing some aspect of the probe. A qualifier column gives an addition word adding to the feature designated in the feature column.

Biological reference table 506 lists interrogated genes or expressed sequence tags (ESTs). There is a primary key column and a column showing the names of genes and expressed sequence tags. It will be appreciated that wherever gene expression is referred to above, the expression of ESTs, or any concentration as measured by polymer probe arrays including oligonucleotide arrays may also be understood to apply.

In operation, bioinformatics database 102 is updated during the various processes depicted in FIG. 1. For example, when an experiment is performed by applying a target sample to a physical chip in accordance with a protocol, an entry is added to experiment table 402 identifying the target sample, physical chip, and protocol. The above description has assumed a database that supports gene expression analysis but the present invention also encompasses databases that support base calling and mutation detection.

It is understood that the examples and embodiments described herein are for illustrative purposes only and that various modifications or changes in light thereof will be suggested to persons skilled in the art and are to be included within the spirit and purview of this application and scope of the appended claims. For example, tables may be deleted, contents of multiple tables may be consolidated, or contents of one or more tables may be distributed among more tables than described herein to improve query speeds and/or to aid system maintenance. Also, the database architecture and data models described herein are not limited to biological applications but may be used in any application. All publications, patents, and patent applications cited herein are hereby incorporated by reference.

What is claimed is:

1. A computer-implemented method for managing information relating to processing of polymer probe arrays, said method comprising:

creating an electronically-stored experiment table, said experiment table storing a record for an experiment, said experiment record comprising a plurality of fields storing at least one of a plurality of data identifiers, including:
a first identifier identifying target sample applied to a polymer probe array chip in said experiment;
a second identifier identifying said polymer probe array chip to which said target sample was applied in said experiment; and
creating an electronically-stored chip table, said chip table storing a record for said polymer probe array chip, said chip record comprising a plurality of fields storing at least one of a plurality of data identifiers, including:
said second identifier identifying said polymer probe array chip, and
a third identifier specifying a layout of polymer probes on said polymer probe array chip.

2. The method of claim 1 further comprising:
performing an experiment wherein said target sample is applied to said polymer probe array chip.

3. The method of claim 1 further comprising:
creating an electronically-stored target table, said target table storing a record for said target sample, said target sample record comprising:
said first identifier identifying said target sample; and
a fourth identifier specifying parameters of preparation of said target sample.

4. The method of claim 1 wherein said polymer probe array chip comprises an oligonucleotide array chip.

5. A computer-implemented method for managing information relating to processing of polymer probe arrays, said method comprising:
storing in an electronically-stored experiment table having a plurality of fields holding at least one of a plurality of data identifiers, for each of a plurality of experiments, a first identifier identifying a target sample applied to an polymer probe array chip in a particular experiment;
storing in said electronically-stored experiment table for each of said plurality of experiments a second identifier identifying said polymer probe array chip to which said target sample was applied in said particular experiment;
storing in an electronically-stored chip table having a plurality of fields holding at least one of a plurality of data identifiers, for each of a plurality of polymer probe array chips, said second identifier identifying a particular polymer probe array chip; and
storing in said electronically-stored chip table for each of said plurality of polymer probe arrays chips a third identifier specifying a layout of polymer probes on said polymer probe array chip.

6. The method of claim 5 further comprising:
storing in an electronically-stored target table, for each of a plurality of target samples, said first identifier identifying a particular target sample; and
storing in said electronically-stored target table, for each of said plurality of target samples, a fourth identifier specifying parameters of preparation of said particular target sample.

7. The method of claim 5 wherein said polymer probe array chip comprises an oligonucleotide array chip.

8. A computer-readable storage medium having stored thereon:
code for creating an electronically-stored experiment table, said experiment table listing for each of a plurality of experiments a plurality of fields storing at least one of a plurality of data identifiers, including:
a first identifier identifying a target sample applied to an oligonucleotide array chip in a particular experiment;
a second identifier identifying said oligonucleotide array chip to which said target sample was applied in said particular experiment; and
code for creating an electronically-stored chip table, said chip table listing for each of a plurality of oligonucleotide array chips a plurality of fields storing at least one of a plurality of data identifiers, including:
said second identifier identifying said particular oligonucleotide array chip; and
a third identifier specifying a layout of oligonucleotide probes on said particular oligonucleotide array chip.

9. The computer-readable storage medium of claim 8 having further stored thereon:
code for creating an electronically-stored target table, said target table listing records comprising:
said first identifier identifying said target sample for one or more of said plurality of experiments; and
a fourth identifier specifying parameters of preparation of said target sample for one or more of said plurality of experiments.

10. A computer-readable storage medium having stored thereon:
an electronically-stored experiment table, said experiment table listing for each of a plurality of experiments a plurality of fields storing at least one of a plurality of data identifiers, including:
a first identifier identifying a target sample applied to an oligonucleotide array chip in a particular experiment;
a second identifier identifying said oligonucleotide array chip to which said target sample was applied in said particular experiment; and
an electronically-stored chip table, said chip table listing for each of a plurality of oligonucleotide array chips a plurality of fields storing at least one of a plurality of data identifiers, including:
said second identifier identifying a particular oligonucleotide array chip; and
a third identifier specifying a layout of oligonucleotide probes on said particular oligonucleotide array chip.

11. A database method for analyzing gene expression information, said method comprising:
providing a first database comprising a first plurality of records, one for each of a plurality of experiments, said records having at least one of a plurality of fields storing:
a first attribute identifying a target sample applied to a polymer probe array chip in said experiment;
a second attribute identifying said polymer probe array chip to which said target sample was applied in said experiment; and
providing a second database comprising a second plurality of records for said polymer probe array chip, said records having at least one of a plurality of fields storing:
said second attribute identifying said polymer probe array chip; and
a third attribute specifying a layout of polymer probes on said polymer probe array chip.

12. The database method for analyzing gene expression information of claim 11, wherein said first database and said second database are relational database tables.

13. The database method for analyzing gene expression information of claim 11, wherein at least one of said first attribute, said second attribute and said third attribute is searchable using a search key.

14. A computer system for analyzing gene expression information, said computer system comprising:

a server, at least one of a plurality of workstations;

a network, interconnecting said server and said at least one of a plurality of workstations, wherein, operatively disposed at said server is a first database comprising a first plurality of records, one for each of a plurality of experiments, said records having at least one of a plurality of fields storing:

a first attribute identifying a target sample applied to a polymer probe array chip in said experiment;

a second attribute identifying said polymer probe array chip to which said target sample was applied in said experiment; and a second database comprising a second plurality of records for said polymer probe array chip, said records having at least one of a plurality of fields storing:

said second attribute identifying said polymer probe array chip; and a third attribute specifying a layout of polymer probes on said polymer probe array chip.

* * * * *